United States Patent [19]
Bagnato et al.

[11] Patent Number: 5,281,236
[45] Date of Patent: Jan. 25, 1994

[54] METHOD AND DEVICE FOR INTRACORPOREAL KNOT TYING

[75] Inventors: V. John Bagnato, Hattiesburg, Miss.; Jeff A. Wilson, Mendon, Mass.

[73] Assignee: Boston Scientific Corporation, Watertown, Mass.

[21] Appl. No.: 903,022

[22] Filed: Jun. 23, 1992

[51] Int. Cl.⁵ ............................................. A61B 17/00
[52] U.S. Cl. ................................ 606/139; 606/148; 604/281; 289/17
[58] Field of Search ............... 606/148, 139; 604/281, 604/284, 164; 289/17, 2

[56] References Cited

U.S. PATENT DOCUMENTS

| | | | |
|---|---|---|---|
| 3,580,256 | 5/1971 | Wilkinson | 606/232 |
| 4,351,333 | 9/1982 | Lazarus et al. | 604/164 |
| 4,641,652 | 2/1987 | Hutterer et al. | 606/ |
| 4,747,840 | 5/1988 | Ladika et al. | 604/281 |
| 4,874,360 | 10/1989 | Goldberg et al. | 604/281 |
| 4,913,683 | 4/1990 | Gregory | 604/281 |
| 4,950,285 | 8/1990 | Wilk | 606/232 |
| 4,957,498 | 9/1990 | Capari et al. | 606/146 |
| 4,961,741 | 10/1990 | Hayhurst | 606/139 |
| 4,986,814 | 1/1991 | Burneg et al. | 604/281 |
| 5,087,263 | 2/1991 | Li | 606/148 |
| 5,098,137 | 3/1992 | Wardall | 289/17 |
| 5,100,418 | 3/1992 | Yoon et al. | 606/139 |
| 5,100,421 | 3/1992 | Christoudias | 606/147 |

OTHER PUBLICATIONS

Endoscopic Suturing and Knot Tying Manual, Ethicon, Inc. 1991.

*Primary Examiner*—Stephen C. Pellegrino
*Assistant Examiner*—Gary Jackson
*Attorney, Agent, or Firm*—Pearson and Pearson

[57] ABSTRACT

A method and device for intracorporeal knot tying. The device comprises an elongated, tubular member formed of a shape memory material for carrying a suture thread through an internal passage. A distal end of the tube is formed with a bight. An outer sheath supports the remaining length of the tube. When a knot is to be formed, a free end of the suture is pulled through the preformed bight. The tube and sheath then move relative to each other to straighten the bight and throw off a knot in the suture thread for subsequent tightening.

24 Claims, 10 Drawing Sheets

METHOD AND DEVICE FOR INTRACORPOREAL KNOT TYING

BACKGROUND OF THE INVENTION

1. Field of the Invention

This invention generally relates to surgical apparatus and procedures and more specifically to a device and method for facilitating intracorporeal knot tying during endoscopic surgical procedures.

2. Description of Related Art

In endoscopic surgical procedures, all the techniques of dissection, cutting, suturing and knot tying must be performed with various elongated instruments that extend through trocars into a cavity of a patient. These instruments include needle holders, tissue graspers, introducers and related instruments for facilitating both extracorporeal and intracorporeal knot tying during endoscopic surgical procedures. Many of these systems utilize preformed loops to form ligatures or needle sutures. However, when preformed loops are used for ligatures, they can only be applied to tissue appendages. They can not, for example, be tied around ducts between two organs. Preformed loops also have a tendency to lock prematurely, that is, before the ligature is finally cinched in place. Extracorporeal knot tying can produce lost insufflation and requires extra time that can extend the overall time for completing a surgical procedure. Transferring a knot from the exterior of the body to the suture site is subject to premature cinching of the knot and the knots are subject to breakage when very thin sutures are used. Intracorporeal knot tying has been difficult to master and is also very time consuming.

The following patents disclose a number of apparatus that have been proposed for facilitating extracorporeal suture tying:

U.S. Pat. No. 3,580,256 (1971) Wilkinson
U.S. Pat. No. 4,961,741 (1990) Hayhurst
U.S. Pat. No. 4,957,498 (1990) Caspari et al
U.S. Pat. No. 5,087,263 (1992) Li
U.S. Pat. No. 5,098,137 (1992) Wardall The Wilkinson patent discloses apparatus that supports a suture in an overlapping loop formation so one end of a suture can be threaded through the loop to form a throw and when pulled tight, a knot. However, in the Wilkinson patent the suture loop must be encased in wax prior to the surgical procedure and a separate casing or structure must be formed independently for each knot.

The Hayhurst patent discloses apparatus in which leading and trailing members guide a pair of suture knots, such as overhand knots, to a tissue surface. The first overhand knot is secured against the tissue as the second knot advances.

The Caspari et al patent disclose a suturing instrument that enables an extracorporeally tied knot to be moved into the body. The apparatus uses a throw stick to advance a knot to the tissue through a cannula.

The Li patent discloses a suture throw holder and rundown system. This apparatus includes a shaft with a cavity and longitudinal and radial slots for receiving a knot and extensions of a suture.

The Wardall patent discloses a structure for forming a knot, extracorporeally. It comprises a fork-like device with first and second tines.

The following patents disclose other proposals for suturing tissue:

U.S. Pat. No. 4,950,285 (1990) Wilk
U.S. Pat. No. 5,100,418 (1992) Yoon et al
U.S. Pat. No. 5,100,421 (1992) Christoudias The Wilk patent discloses a specially formed suture having at one end a preformed loop, a specially formed adjacent surface and a special capture structure.

The Yoon et al patent discloses a suture tie and applicator which holds preformed suture ties comprising rigid or semi-rigid segments of sutures disposed within and extending out of the distal end of a tubular locking member. The locking member displaces along the tie until it closes the open side of a tissue receiving area.

The Christoudias patent discloses a suture assembly that includes a needle holder, needle transporter and a needle suture.

None of the foregoing references disclose apparatus that enables or can be adapted to enable a surgeon to tie knots intracorporeally. Consequently a typical intracorporeal knot tying method involves wrapping one free end of a suture thread into a series of loops around a needle holder proximate a tissue site. Then the surgeon uses a grasping instrument to remove the loops from the needle holder without dropping a loop. Next the surgeon picks up the other free end of the suture thread through the loops. Finally the surgeon manipulates both ends of the suture tie to advance the resulting knot toward the tissue and to tighten the knot. Then, as this is a form of slip knot, the procedure is repeated.

As will be apparent, this process is time consuming and complex. It requires great dexterity by the surgeon and is difficult to master. Various instruments must be withdrawn after the suture has passed through the tissue and this further complicates the procedure. Moreover, each time an instrument is replaced, any gas being used in conjunction with the procedure can escape through an open trocar. Notwithstanding these problems, surgeons continue to use either of these extracorporeal or intracorporeal knot tying procedures.

SUMMARY

Therefore it is an object of this invention to provide a new method and device for facilitating intracorporeal suture tying.

Still another object of this invention is to provide a new method and device for facilitating intracorporeal suture tying that is adapted for producing multiple knots in situ.

Still another object of this invention is to provide a new method and device for facilitating intracorporeal suture tying in locations with limited access.

Yet another object of this invention is to provide a new method and device for facilitating intracorporeal suture tying that minimizes the difficulty of and the time required for tying such intracorporeal suture knots.

In accordance with this invention, a device for facilitating a tying of an intracorporeal suture includes an elongated flexible tube formed of a shape memory material. The tube is formed with a bight at the distal end and carries the suture thread. A knot is formed by drawing a free end of the suture through a loop formed by the bight and then straightening the bight to produce a knot in the suture thread.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
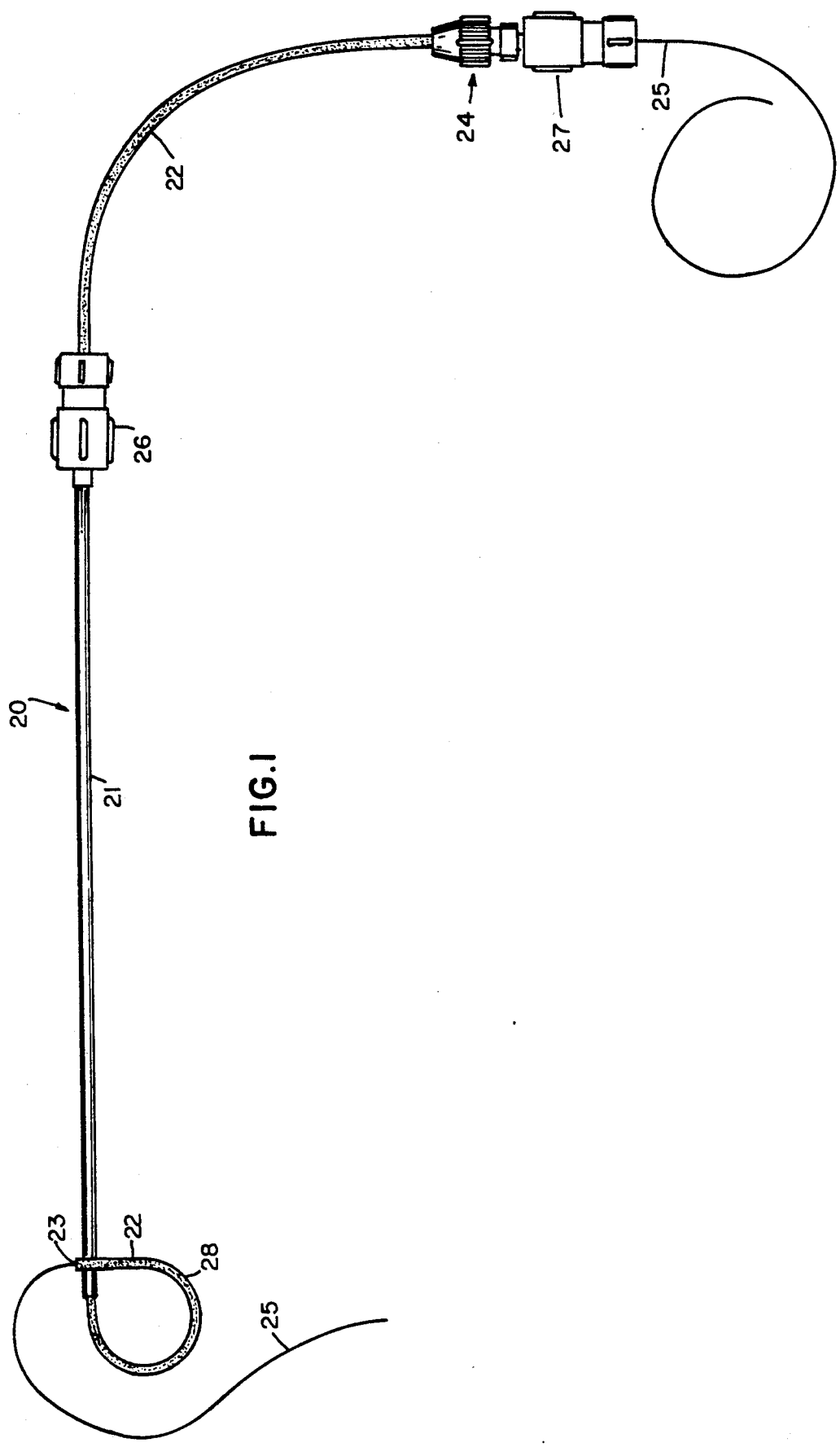
FIG. 1 is a plan view of a suture tying device constructed in accordance with this invention particularly adapted for tying ligature sutures.

FIG. 1 discloses a intracorporeal knot tying device 20 constructed in accordance with this invention that comprises sheath 21 and an elongated tube or catheter 22. The catheter 22 has a distal end 23 and a proximal end 24. The catheter 22 carries a suture thread 25.

The proximal end of the sheath 21 terminates with a Leur lock fitting 26 while the proximal end 24 of the catheter 22 terminates in a Leur lock fitting 27 in this particular embodiment. The Leur lock fittings 26 and 27 provide structure for manipulating the position of the sheath 21 and catheter 22 with respect to a particular intracorporeal site or with each other.

As apparent from FIG. 1, the sheath 21 supports only a portion of the catheter. The catheter 22 slides freely within the sheath 21 whenever the Leur lock fitting 26 is released. Similarly the suture thread 25 slides freely within the catheter 22 when the Leur lock fitting 27 is released.

The catheter 22 is formed of a composition having shape memory so the distal portion of the catheter 22 can be formed into and retain the position of a bight 28. More specifically, the distal end portion 23 of the catheter 22 is bent by substantially 270° and partially crosses an intermediate portion of the sheath 21.

A number of compositions have shaped memories. Spring steel and nitinol are examples of metals with shape memory. Polyethylene and polypropylene are examples of plastic materials having shape memory. Percuflex ® materials available from the assignee of the present invention and C-flex ® materials available through Concept Business Polymers are specific examples of such plastic materials. The catheter 22 may also comprise a composite of plastic and metals such that the overall composite has shape memory.

Thus, the catheter 22 can be composed of any material that has shape memory and that allows bight 28 to be straightened under a reasonable force and then to return to the form of the bight 28 when the external force is released. The composition also should be compatible with a medical environment.

The intracorporeal knot tying device 20 constructed as shown in FIG. 1 enables a physician to release the Leur lock fitting 26 and advance the sheath 21 distally over the catheter 22 and straighten the catheter 22 at the bight 28. If the sheath 21 moves proximally with respect to the catheter 22, the distal end 23 emerges from the sheath 21 and reforms the bight 28 shown in FIG. 1.

Figure 2:
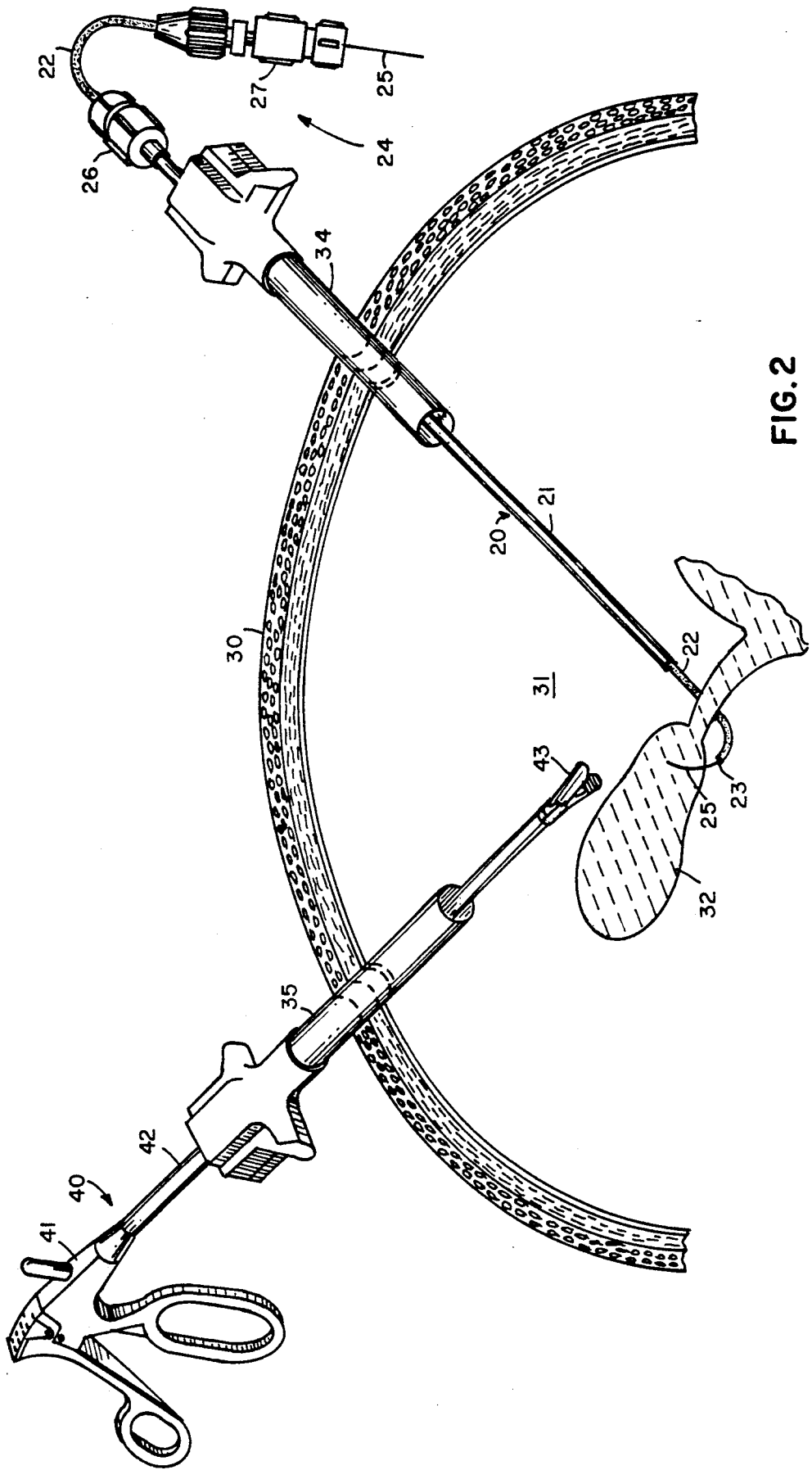
FIG. 2 is a schematic view that is useful in understanding the operation of this invention.

FIG. 2 discloses, in schematic form, an application of the knot tying device 20 for use with a ligature. For purposes of explanation, FIG. 2 depicts a human torso 30 and an internal cavity 31 surrounding a gall bladder 32 and cystic duct 33. A trocar 34 carries the device 20 including the sheath 21, the catheter 22 and suture thread 25. Another trocar 35 penetrates the torso 30 to provide an access for a grasper 40 having a handle 41, an intermediate shaft 42 and grasper jaws 43 at the distal end thereof. Although not shown in this particular embodiment, a surgeon would view the cavity 31 through an endoscope placed proximate the cavity 31 through another access port.

In FIG. 2, the sheath 21 is positioned along the catheter 22 toward the distal end 23 thereby to straighten the catheter 22 partially. This opens the bight 28 (shown in FIG. 1) and allows a physician to manipulate the device 20 and to position the suture thread 25 on one side of the portion to be ligatured, in this particular example the cystic duct 33. The physician then can utilize the grasper 40 and capture the suture thread 25 with the jaws 43 to hold the distal end of the suture thread 25 in a stable position. If the physician then releases the Leur lock fitting and withdraws both the sheath 21 and the catheter 22 proximally, the suture thread 25 pulls from the distal end 23. If, after the distal end 23 is clear of the cystic duct 33, the physician further retracts the sheath 21 with respect to the catheter 22, the catheter 22 will reform the bight 28 as shown in FIG. 3.

Figure 3:
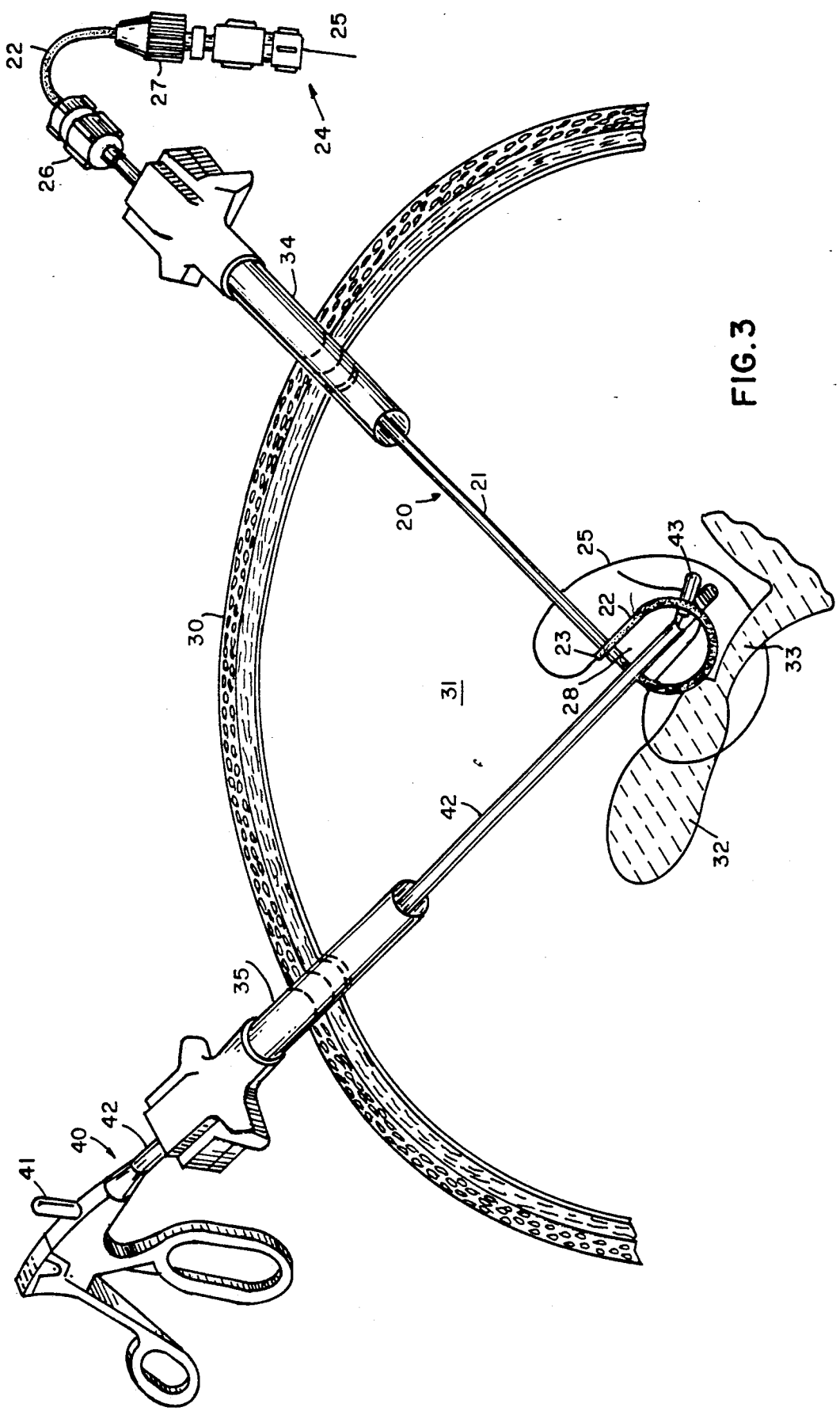
FIG. 3 is another schematic view that is helpful in understanding this invention.

More specifically, FIG. 3 depicts the relationship of the various instruments at a next stage in the procedure. The physician has subsequently extended the grasper 40 and led the end of the suture thread 25 through the bight 28. Next the physician will release the end of the suture thread 25, partially withdraw the grasper 41 and then extend it to grasp the end of the suture thread 25 on the other side of the bight 28. In other circumstances it may be possible to form the ligature by extending the grasping jaws 43 through the bight 28, grasping the end of the suture thread 25 and retracting the jaws 43 back through the bight 28 to complete a loop.

Figure 4A:
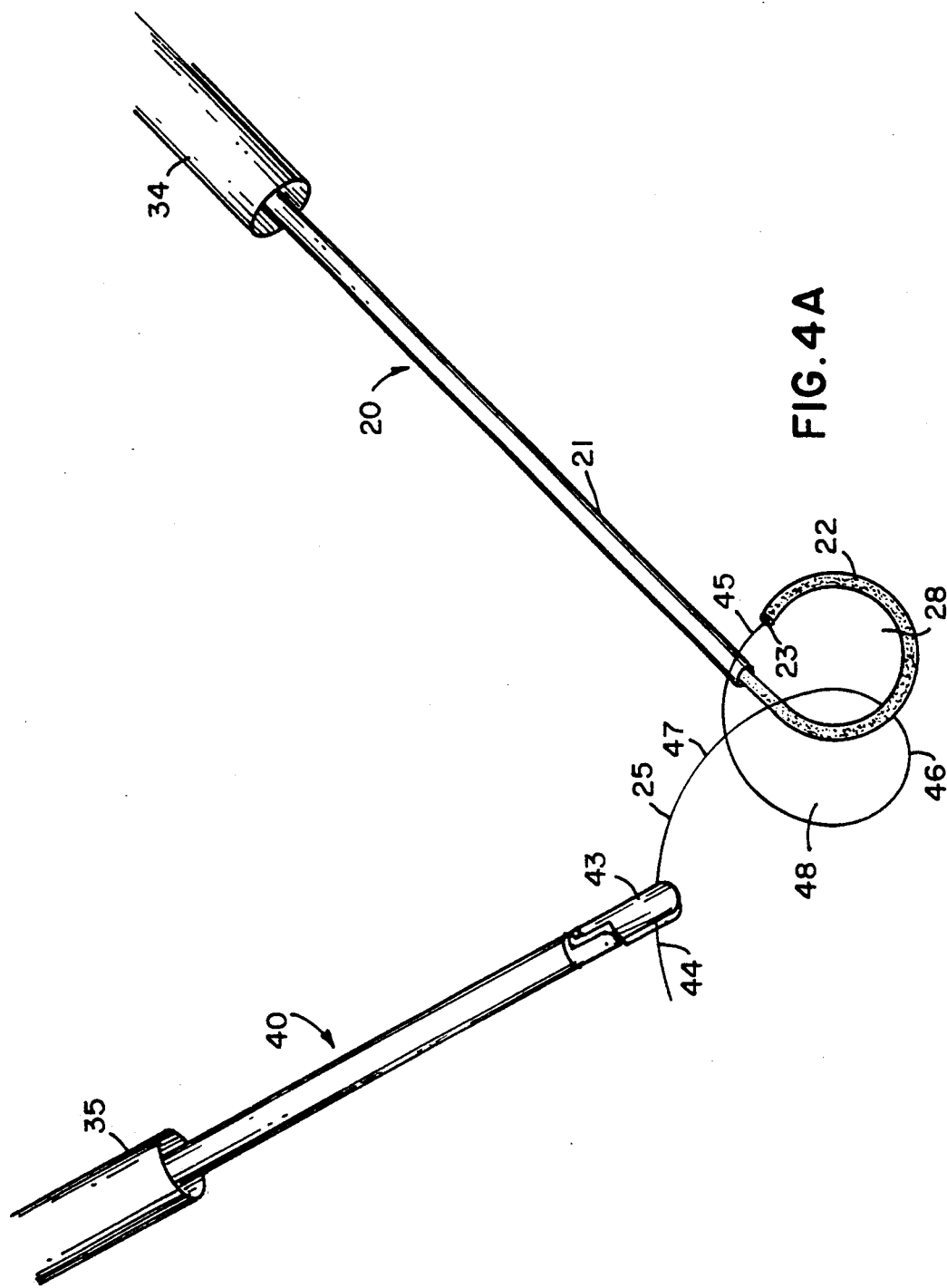
FIGS. 4A through 4E depict a method for using the device shown in FIGS. 1 through 3.

When the physician completes the specific operations in FIGS. 2 and 3 or other similar operations, the device 20, suture 25 and grasping jaws 43 can produce a configuration as shown by the simplified view in FIG. 4A. The grasping jaws 43 on the grasper 40 clamp a distal end 44 of the suture thread 25. A portion 45 of the suture thread 25 extends from the distal end 23 of the catheter 22 and overlies the sheath 21. An adjacent portion 46 passes through the bight 28; and a final portion 47 overlies the section 46. Sections 46 and 47 therefore form a hitch or loop 49 around the catheter 22.

Figure 4B:
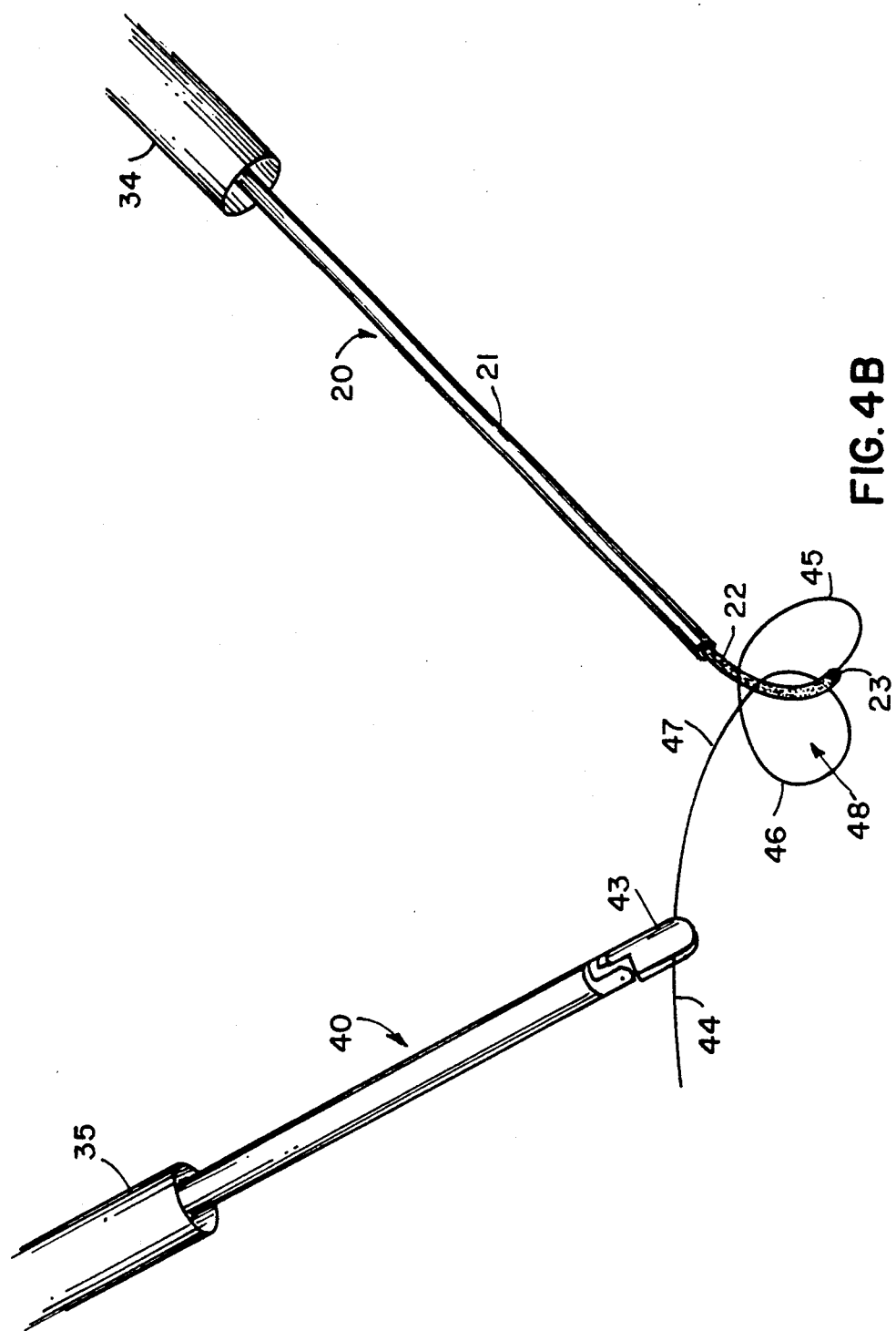
Figure 4C:
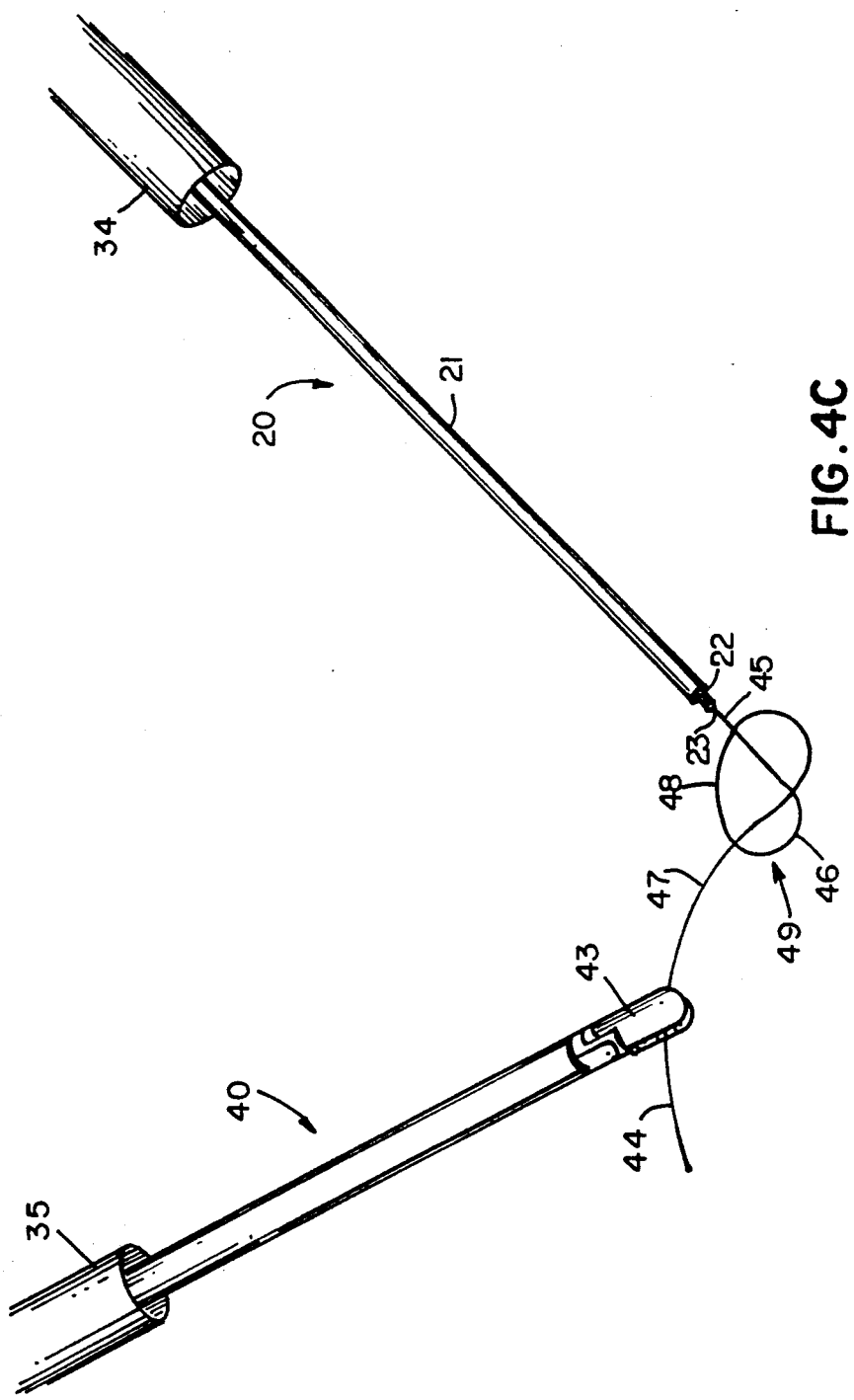

Referring to FIG. 4B, the surgeon holds the distal end 44 of the unit in place with the grasper 40 and withdraws the catheter 22 into the sheath 21 along with the suture thread 25. Thereupon the portion 45 draws through the loop 48 to produce a knot 49 in the suture 25 as shown in FIG. 4C. Further manipulation of the device 20 and the grasper 40 allows the knot 49 to tighten the loop 48 around a vessel such as the duct 33 in FIG. 3. From this it will be obvious that the vessel need not be an appendage as would be required if a preloop were formed and transferred along an introducer to the site.

Figure 4D:
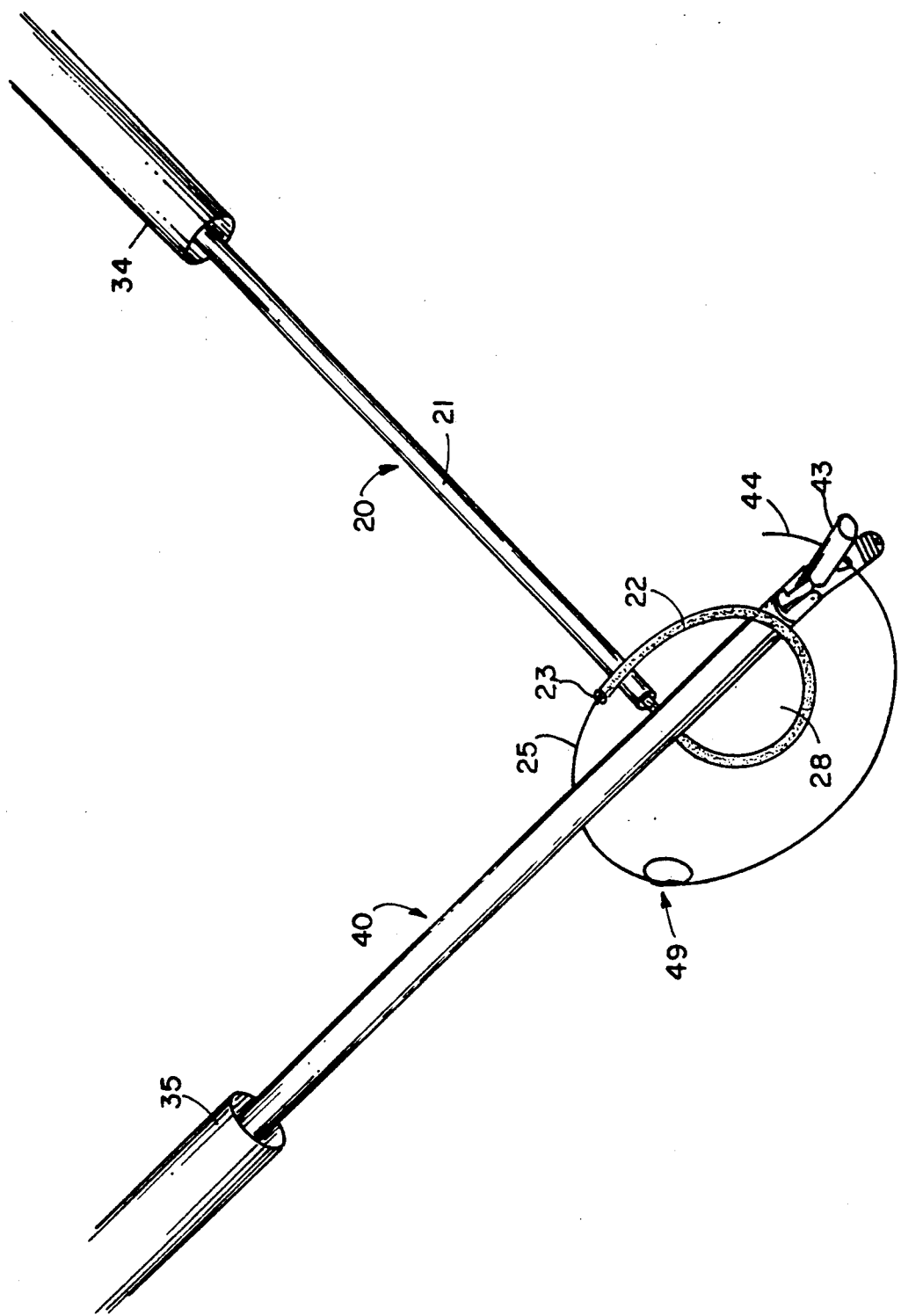
Figure 4E:
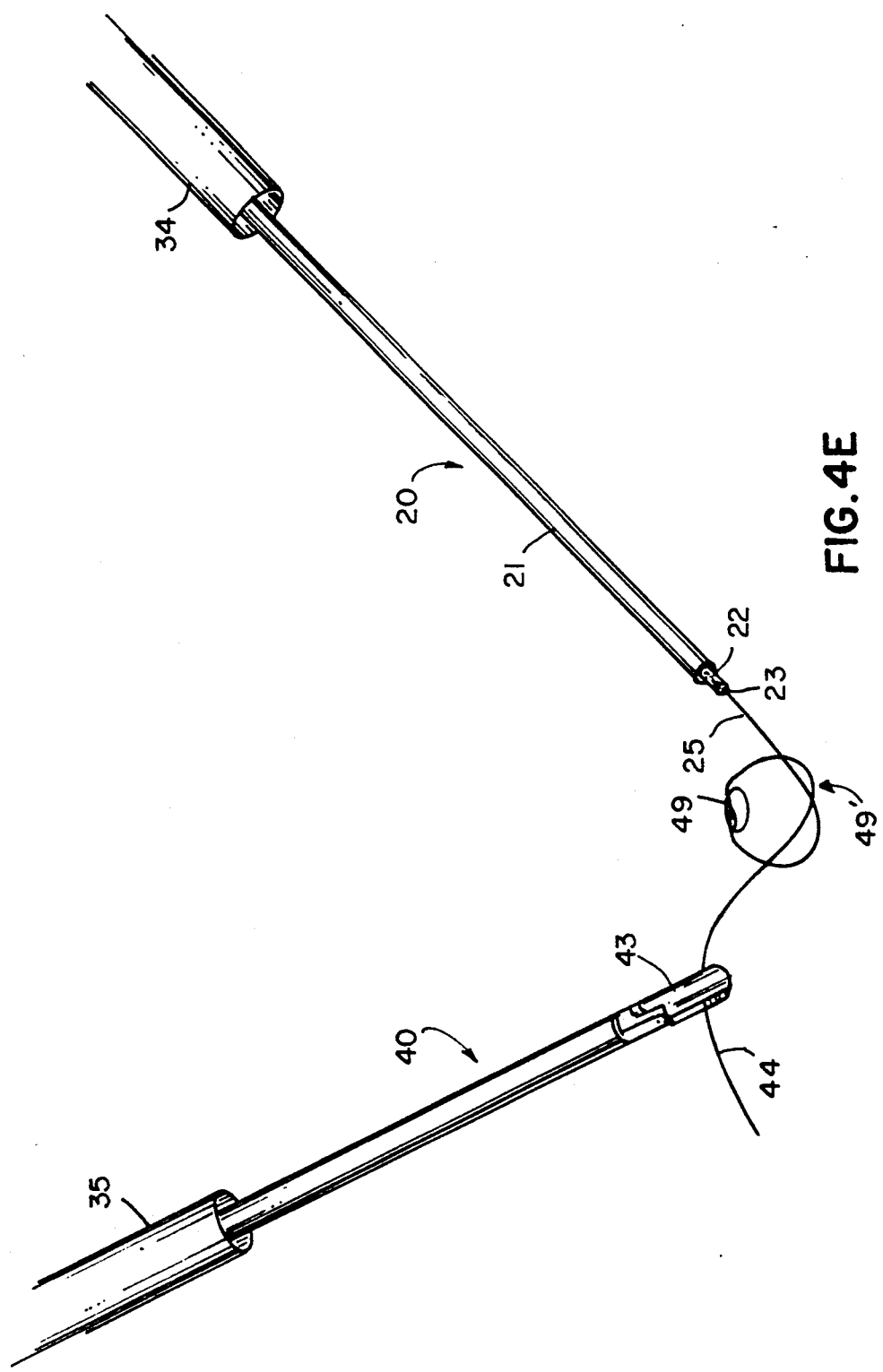

Moreover, once a first overhand knot is formed, the system facilitates the formation of a second knot as shown in FIGS. 4D and 4E. Referring specifically to FIG. 4D, the physician extends the catheter 22 distally to reform the bight 28. This occurs because the catheter 22 has shape memory. Next the physician moves the grasper 40 to reposition the free end 44 of the suture thread 25 in line with the bight 28. Then the physician releases the grasping jaws 40 and extends them through the bight 28. The physician again grasps the free end 44 of the suture 25 in the jaws 43 and pulls the free end through the bight 28.

Referring to FIG. 4E, the physician completes the knot by holding the distal end 44 of the suture 25 in a stable position with the grasper 40. Next the sheath 21 advances distally to straighten the bight 28 and throw off another knot, in this case another overhand knot 49'. When the knots 49 and 49' tighten, they form a square knot.

It has been found that the intracorporeal knot tying device 20 minimizes the tension applied to the suture thread 25. Consequently, the device 20 shown in FIG. 1 enables fine suture threads, in the order of 1mm or so, to be manipulated without breakage. It is also possible to construct such a device with a minimal outer diameter thereby to facilitate its use with trocars of minimal diameter.

Therefore in accordance with several objects of this invention, the intracorporeal knot tying device 20 provides an apparatus for facilitating the intracorporeal knotting of ligatures. This device and method are particularly adapted for use in areas of limited access because only limited lateral motion of the device 21 is required. All other motion generally occurs along the entrance axis for the device 20 that the trocar 34 establishes. Minimal motions are required of the grasping handle 40.

Furthermore, it has been found that this method is readily learned. Physicians can tie knots more rapidly than was possible with prior devices or procedures. Finally, as shown in FIGS. 4A through 4E, it is possible to use this device intracorporeally to form multiple overhand knots at a single site. Other knots can also be tied.

Figure 5:
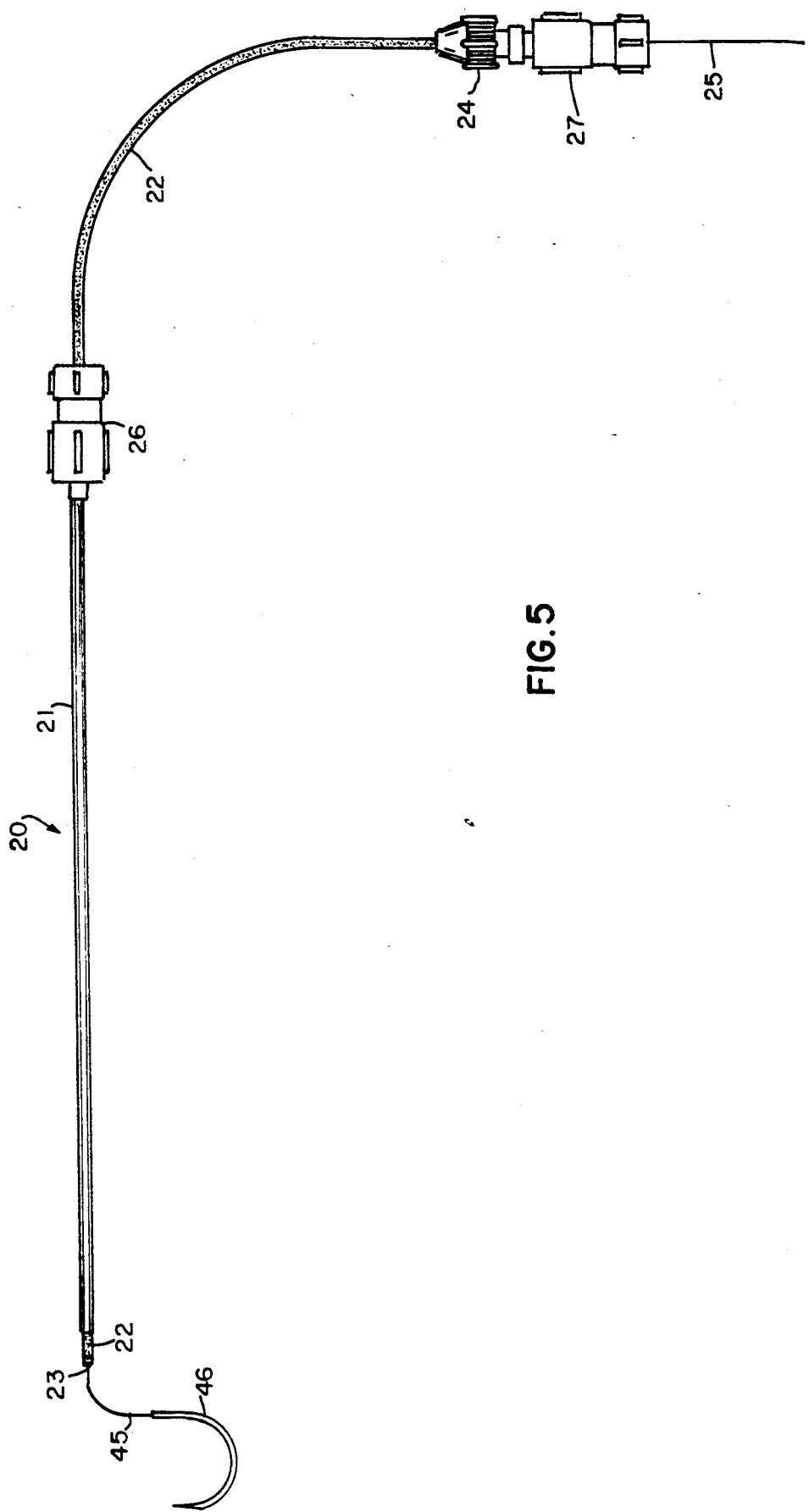
FIG. 5 is a plan view of a suture tying device constructed in accordance with this invention and adapted for use with a needle suture.

This apparatus is also useful with needle sutures such as shown in FIG. 5. where like numbers refer to like elements of the intracorporeal knot tying device 20 shown in FIG. 1. In the embodiment in FIG. 5, the suture comprises a suture thread 50 and a needle 51 at the distal end. The suture thread 50 extends through the catheter 22 in the device 20 and rides in a sheath 21. Leur lock fittings 26 and 27 at the proximal end of the device 20 provide means for stabilizing the system and provide a means for manipulating the device 20 in the same manner as was described with respect to FIG. 1.

Figure 6:
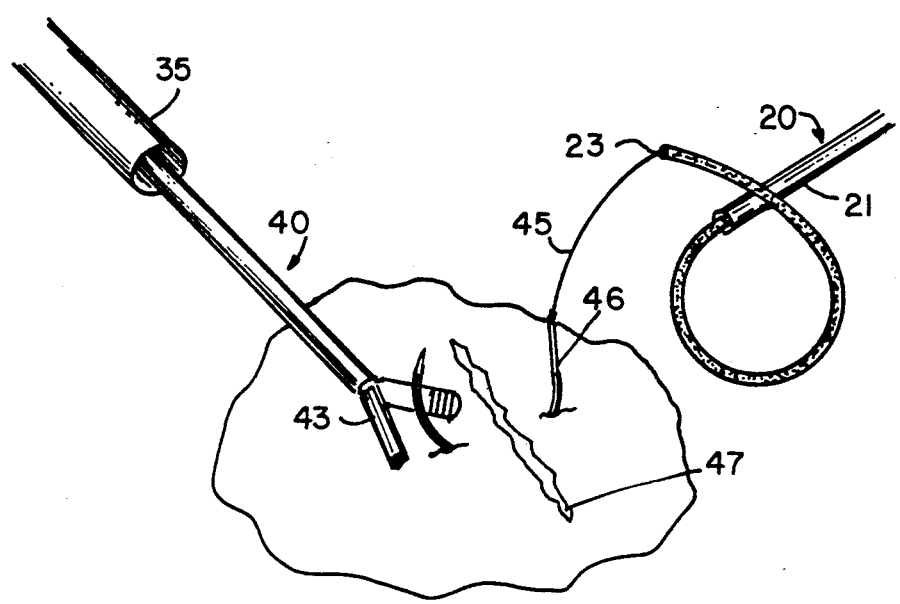
FIG. 6 depicts in schematic form, one aspect of the operation of the device in FIG. 5.

FIG. 6 depicts a suture 50 that joins two pieces of tissue 52 separated along a tear 53. Specifically the physician uses the grasper 40 to lock the jaws 43 onto the curved needle 51 and penetrate the tissue 52 in an arcuate path spanning the tear 53. As shown in FIG. 6 the physician can grasp the end of the needle 51 in the jaws 43 and pull the needle 51 through the tissue 52 carrying the suture thread 50. When a sufficient amount of suture thread 50 has been pulled past the tear 53, the needle 51 is laid on the tissue 52.

Figure 7:
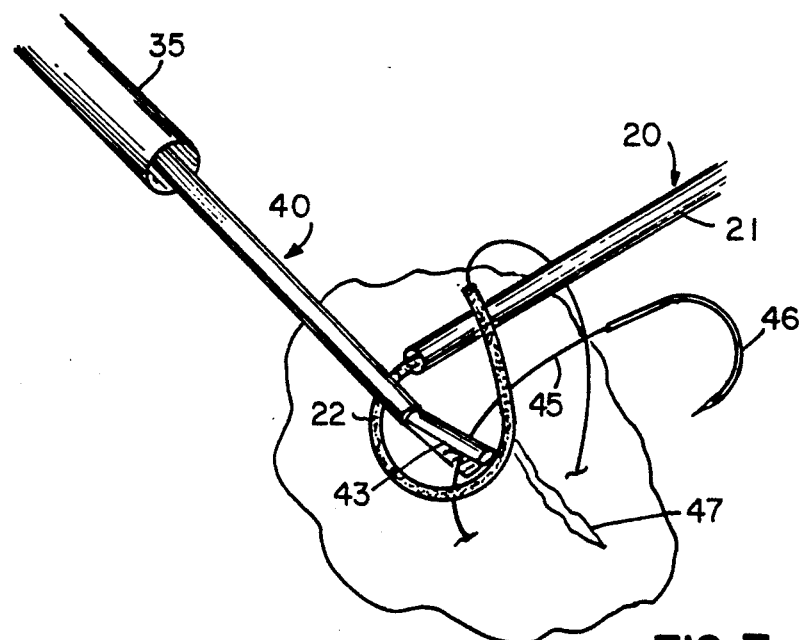
FIG. 7 illustrates another aspect of the operation of the device in FIG. 5.

As shown in FIG. 7, the physician redirects the grasping jaws 43 through the bight 28 formed by the catheter 22 to grasp the needle 51 or the suture thread 50 adjacent the needle 51. The physician withdraws the needle 51 and adjacent thread 50 through the bight 28 to form a loop or hitch around the catheter 21. Thereafter the physician can proceed with a method as shown in FIGS. 4A through 4E to produce one or more overhand or other knots at the tear 53.

Therefore in accordance with this invention, there has been disclosed a device for facilitating intracorporeal knot tying. The device is particularly adapted for endoscopic surgery and is simple and reliable. Its operation is readily mastered. It can produce a knot tying operation that is significantly faster than previous extracorporeal or intracorporeal procedures. Moreover, the device enables a physician to exercise good control over the knot tying operation.

As described, the sheath 21 and catheter 22 can be composed of a wide range of compositions. The Leur locks 26 and 27 are shown as examples of manipulators. The actual manipulating mechanism may be more complex. Consequently although this invention has been disclosed in terms of certain embodiments, it will be apparent that many modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. A device for facilitating the tying of a suture at a distal, intracorporeal location by manipulation at a proximal location comprising:
   A. an elongated flexible tube means formed of a shape memory material for supporting a suture between the proximal and distal locations, said tube being formed with a bight at the distal end and thereby forming a loop in the suture,
   B. elongated sheath means for overlying said tube means and being displaceable with respect to said tube means whereby displacement of said sheath means to the distal end of said tube means straightens said bight and proximal displacement of said sheath means enables said tube means to reform said bight, and
   C. manipulation means for moving said tube means and said sheath means relative to the distal location and to each other.

2. An intracorporeal knot tying device as recited in claim 1 wherein said manipulation means comprises first and second manipulators at the proximal ends of said tube means and of said sheath respectively.

3. An intracorporeal knot tying device as recited in claim 2 wherein said tube means comprises an elongated flexible tube formed of a material characterized by a shape memory.

4. An intracorporeal knot tying device as recited in claim 3 wherein said flexible tube material is of shape memory metals and metal alloys.

5. An intracorporeal knot tying device as recited in claim 3 wherein said flexible tube material comprises a plastic material having shape memory characteristics.

6. An intracorporeal knot tying device as recited in claim 3 wherein said flexible tube material comprises a composite of plastic and metal materials wherein said composite has shape memory characteristics.

7. An intracorporeal knot tying device as recited in claim 3 wherein said sheath is formed of a metal.

8. An intracorporeal knot tying device as recited in claim 3 wherein said sheath is formed of stainless steel.

9. An intracorporeal knot tying device as recited in claim 1 wherein said manipulation means comprises first and second manipulators at the proximal ends of said tube means and of said straightening means, respectively.

10. An intracorporeal knot tying device as recited in claim 1 wherein said material is taken from a group of metals and metal alloys characterized by having shape memory.

11. An intracorporeal knot tying device as recited in claim 1 wherein said material is of thermoplastic material having shape memory.

12. An intracorporeal knot tying device as recited in claim 1 wherein said material comprises a composite having shape memory characteristics.

13. A method for tying a suture at a distal, in situ location by manipulation at a proximal location wherein the suture is held in an elongated, flexible tube, said method comprising the steps of:
   A. forming a bight at the distal end of the tube proximate the in situ location,
   B. displacing the distal end of the suture through the bight,
   C. straightening the bight end to form a loop in the suture externally of the tube thereby to form a knot in the suture.

14. An intracorporeal knot tying method as recited in claim 13 wherein the tube is composed of a material with shape memory and is carried in a sheath, said straightening comprising a step of displacing the sheath distally with respect to the tube thereby to straighten the bight.

15. An intracorporeal knot tying method as recited in claim 14 additionally comprising the step of displacing the sheath proximally after forming a knot thereby to enable the tube to reform a bight at the distal end.

16. An intracorporeal knot tying method as recited in claim 13 wherein said displacing step includes positioning the bight to enable grasping means to extend through the bight to grasp the distal end of the suture, moving the distal end of the grasping means through the bight, grasping the distal end of the suture and withdrawing the distal suture end through the bight.

17. An intracorporeal knot tying method as recited in claim 16 wherein the tube is composed of a material with shape memory and is carried in a sheath, said straightening step comprising the steps of holding the distal end of the suture at a stable position with the grasping means, holding the distal end of the tube at a stable position and displacing the sheath distally with respect to the tube thereby to straighten the bight and form a knot in the suture.

18. An intracorporeal knot tying method as recited in claim 17 additionally comprising the steps of applying tension to the portions of the suture extending from the knotted portion thereby to tighten the knot.

19. A device for facilitating the tying of a suture at a distal, intracorporeal location by manipulation at a proximal location comprising:
   A. an elongated flexible tube means formed of a shape memory material for supporting a suture between the proximal and distal locations, said tube being formed with a bight at the distal end and having a predetermined length and thereby forming a loop in the suture,
   B. elongated sheath means for engaging said tube means and being displaceable with respect to said tube means whereby displacement of said sheath means to the distal end of said tube means straightens said bight and proximal displacement of said sheath means enables said tube means to reform said bight, said elongated sheath means having a length that is less than the predetermined length, and
   C. manipulation means for moving said tube means and said sheath means relative to the distal location and to each other.

20. A device for facilitating the tying of a suture at a distal, intracorporeal location by manipulation at a proximal location comprising:
   A. an elongated flexible tube means formed of a shape memory material for supporting a suture between the proximal and distal locations, said tube being formed with a bight at the distal end and having a predetermined length and thereby forming a loop in the suture,
   B. elongated sheath means for overlying said tube means and being displaceable with respect to said tube means whereby displacement of said sheath means to the distal end of said tube means straightens said bight and proximal displacement of said sheath means enables said tube means to reform said bight, said sheath means having a length that is less than the predetermined length, and
   C. manipulation means for moving said tube means and said sheath means relative to the distal location and to each other.

21. An intracorporeal knot tying device as recited in claim 20 wherein said manipulation means comprises first and second manipulators at the proximal ends of said tube means and of said straightening means, respectively.

22. An intracorporeal knot tying device as recited in claim 20 wherein said material is of shape memory metals and shape memory metal alloys.

23. An intracorporeal knot tying device as recited in claim 20 wherein said material is a thermoplastic material having shape memory.

24. An intracorporeal knot tying device as recited in claim 20 wherein said material comprises a plastic and metal composite having shape memory characteristics.

* * * * *